United States Patent
Palti et al.

(10) Patent No.: US 9,724,067 B2
(45) Date of Patent: Aug. 8, 2017

(54) TRANSTHORACIC PULMONARY DOPPLER ULTRASOUND FOR EVALUATING THE HEART OR LUNG VIA DOPPLER SHIFT POWER SPECTRUM

(75) Inventors: Yoram Palti, Haifa (IL); Meytal Lempel, Ramot Menashe (IL); Ayelet Kanter, Yokneam (IL); Yoram Wasserman, Haifa (IL)

(73) Assignee: Echosense Jersey Limited, St. Helier (JE)

( * ) Notice: Subject to any disclaimer, the term of this patent is extended or adjusted under 35 U.S.C. 154(b) by 1880 days.

(21) Appl. No.: 12/912,988

(22) Filed: Oct. 27, 2010

(65) Prior Publication Data
US 2011/0125023 A1 May 26, 2011

Related U.S. Application Data

(60) Provisional application No. 61/255,322, filed on Oct. 27, 2009, provisional application No. 61/326,133, (Continued)

(51) Int. Cl.
*A61B 8/08* (2006.01)
*A61B 8/02* (2006.01)
(Continued)

(52) U.S. Cl.
CPC .............. *A61B 8/08* (2013.01); *A61B 8/0883* (2013.01); *A61B 8/488* (2013.01); *A61B 8/5223* (2013.01);
(Continued)

(58) Field of Classification Search
CPC .... A61B 8/02; A61B 8/06; A61B 8/08; A61B 8/0883; A61B 8/488
(Continued)

(56) References Cited

U.S. PATENT DOCUMENTS 6,368,286 B1    4/2002  Whitman et al.
6,520,911 B1 *  2/2003  Wen .............................. 600/437
(Continued)

FOREIGN PATENT DOCUMENTS

WO       2008073560       6/2008

OTHER PUBLICATIONS

Lichtenstein, D.A., et al. Relevance of lung ultrasound in the diagnosis of acute respiratory failure. The Blue Protocol. CHEST, 2008; 134:117-125.*
(Continued)

*Primary Examiner* — Serkan Akar
(74) *Attorney, Agent, or Firm* — Potomac Law Group, PLLC

(57) ABSTRACT

Operation of a patient's heart or lungs may be analyzed by transmitting ultrasound energy into the patient's lung, and detecting Doppler shifts of reflected ultrasound induced by moving borders between blood vessels in the lung and air filled alveoli that surround the blood vessels. Movement of the border is caused by pressure waves in the blood vessels that result in changes in diameter of those blood vessels. The detected Doppler shifts are processed with an algorithm designed to increase signal from the moving border with respect to other reflected ultrasound signals and the results are then displayed.

16 Claims, 16 Drawing Sheets

Related U.S. Application Data filed on Apr. 20, 2010, provisional application No. 61/405,454, filed on Oct. 21, 2010.

(51) Int. Cl.
*A61B 8/06* (2006.01)
*A61B 8/00* (2006.01)

(52) U.S. Cl.
CPC . *A61B 8/02* (2013.01); *A61B 8/06* (2013.01); *A61B 8/543* (2013.01)

(58) Field of Classification Search
USPC .......................................................... 600/453
See application file for complete search history.

(56) References Cited

U.S. PATENT DOCUMENTS

2003/0055331 A1* 3/2003 Kotmel et al. ................ 600/410
2005/0080329 A1* 4/2005 Uchibori ...................... 600/407
2006/0052704 A1* 3/2006 Baba et al. ................... 600/453
2009/0143678 A1* 6/2009 Keast ...................... A61B 8/06
600/439
2010/0010354 A1* 1/2010 Skerl et al. ................... 600/459

OTHER PUBLICATIONS

Islam et al, Emergency Bedside Ultrasound to Detect Pneumothorax by Islam et al, Acad Emerg Med Jul. 2003, vol. 10, No. 7.*
Ginghina et al, Respiratory maneuvers in echocardiography: a review of clinical applications, Cardiovascular Ultrasound, 2009, 7:42, p. 1-20.*
Hawkins et al, Heart failure and chronic obstructive pulmonary disease: diagnostic pitfalls and epidemiology, Eur J Heart Fail. Feb. 2009; 11(2): 130-139.*
Tony F. Chan, Active Contours Without Edges; IEEE Transactions on Image Processing, vol. 10. No. 2, Feb. 2001.
Partial International Search in corresponding application PCT/IB2010/002743.

* cited by examiner

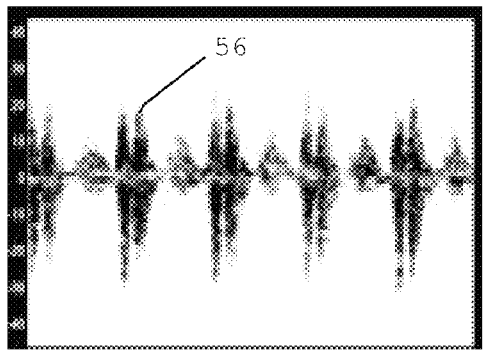 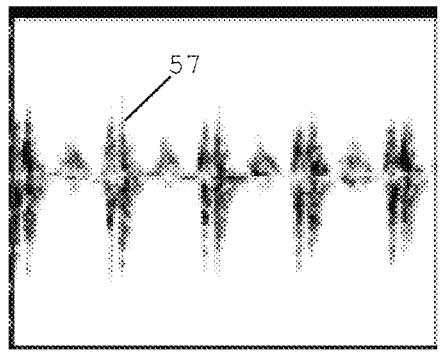
FIG. 5B  FIG. 5C
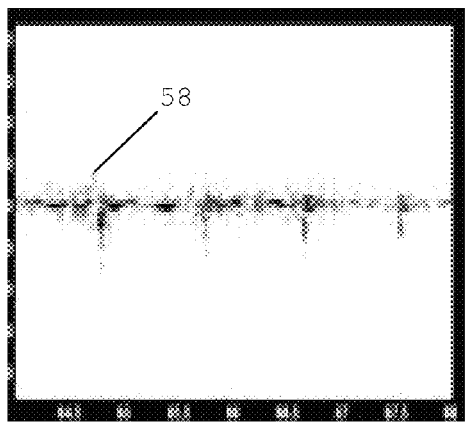 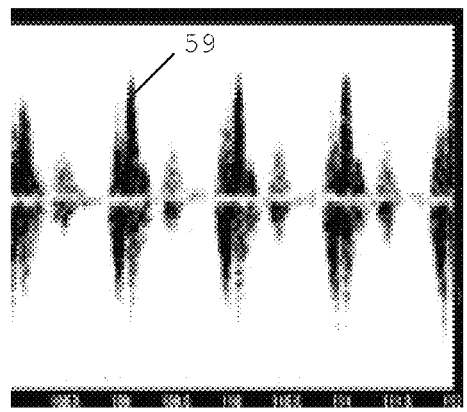
FIG. 5D  FIG. 5E

TRANSTHORACIC PULMONARY DOPPLER ULTRASOUND FOR EVALUATING THE HEART OR LUNG VIA DOPPLER SHIFT POWER SPECTRUM

CROSS REFERENCE TO RELATED APPLICATIONS

This Application claims the benefit of U.S. Provisional Application 61/255,322, filed Oct. 27, 2009, U.S. Provisional Application 61/326,133, filed Apr. 20, 2010, and U.S. Provisional Application 61/405,454, filed Oct. 21, 2010, each of which is incorporated herein by reference.

BACKGROUND

The use of ultrasound Doppler for Spectral measurement of blood flow velocity in arteries and veins is well established. One widely used procedures for making such measurements is based on three typical stages: an initial identification of the target area (where flow is to be measured) using ultrasound imaging; placement of a marker on the appropriate position on the image; and switching the echo device from Imaging mode to Spectral Doppler Examination mode in order to display the flow velocities in real-time. This procedure can be used, for example, to measure the blood flow in a pulmonary vein.

Another procedure, which is relatively new, is used for Trans Cranial Doppler (TCD) measurements, as well as some peripheral vascular studies. In this procedure the ultrasound beam is directly aimed at the known location of the target, without relying on imaging. As the structure and positioning of the human skull and its constituents are relatively fixed and known, specific vessels such as the arteries of the circle of Willis, at the base of the brain, are being studied in this procedure by echo Doppler alone (i.e. without imaging). The fact that the flow velocity measurements can be made without imaging enables one to do the measurements through the bones of the skull that attenuate and scatter the ultrasound beam to such an extent that practical images cannot be obtained.

While trans-cranial Doppler measurements are now in routine use to study structures in the brain, applying this technology trans-thoracically monitor pulmonary vessels was heretofore considered impossible. This is due to the fact that the lungs contain numerous air pockets that attenuate and scatter ultrasound far more than bone. In view of this, except for the initial, large, segments of the pulmonary vessels that are not masked by lung tissue, arterial and venous flow velocity in the pulmonary vasculature and the lung tissue itself have not been studied by Doppler ultrasound.

SUMMARY

One aspect of the invention is directed to a method of evaluating the functionality of a patient's heart or lungs. This method includes the steps of transmitting ultrasound energy into the patient's lung and detecting Doppler shifts of reflected ultrasound induced by moving borders between blood vessels in the lung and air filled alveoli that surround the blood vessels. Movement of the border is caused by pressure waves in the blood vessels that result in changes in diameter of those blood vessels. The detected Doppler shifts are processed with an algorithm designed to increase signal from the moving border with respect to other reflected ultrasound signals and to output the processed power and velocity data which is then displayed.

Another aspect of the invention is directed to a method of evaluating the functionality of a patient's heart or lungs. This method includes the steps of obtaining, using an ultrasound probe that is aimed at the patient's lung, Doppler ultrasound power and velocity data for a period of time that corresponds to at least one cardiac cycle. The power and velocity data obtained in the obtaining step are processed using at least one noise reduction algorithm, and the processed power and velocity data are displayed. An abnormality in at least one of (a) a feature on the display that corresponds to systolic ventricular contraction, (b) a feature on the display that corresponds to ventricular relaxation, (c) a feature on the display that corresponds to a diastolic rapid filling phase, (d) a feature on the display that corresponds to diastasis, and (e) a feature on the display that corresponds to atrial contraction is correlated with an abnormal condition of the patient's heart or lungs.

Another aspect of the invention is directed to a method of evaluating the functionality of a patient's heart or lungs. This method includes the steps of obtaining, using an ultrasound probe that is aimed at the patient's lung, Doppler ultrasound power and velocity data for a period of time that corresponds to at least one cardiac cycle. The power and velocity data obtained in the obtaining step are processed using at least one noise reduction algorithm. After processing, the results are checked for abnormalities in (a) a feature of the processed power and velocity data that corresponds to systolic ventricular contraction, (b) a feature of the processed power and velocity data that corresponds to ventricular relaxation, (c) a feature of the processed power and velocity data that corresponds to a diastolic rapid filling phase, (d) a feature of the processed power and velocity data that corresponds to diastasis, and (e) a feature of the processed power and velocity data that corresponds to atrial contraction. An absence of abnormalities is correlated with a normal condition of the patient's heart or lungs.

Another aspect of the invention is directed to a method of evaluating the functionality of a patient's heart or lungs. This method includes the steps of obtaining, using an ultrasound probe that is aimed at a first position of the patient's lungs, a first set of Doppler ultrasound power and velocity data for a period of time that corresponds to at least one cardiac cycle and obtaining, using an ultrasound probe that is aimed at a second position of the patient's lungs, a second set of Doppler ultrasound power and velocity data for a period of time that corresponds to the at least one cardiac cycle. A first output is generated by processing the first set of data using at least one noise reduction algorithm, and a second output is generated by processing the second set of data using at least one noise reduction algorithm.

BRIEF DESCRIPTION OF THE DRAWINGS

FIGS. 5B-E are TPD outputs for normal breathing and during various respiratory maneuvers.

DESCRIPTION OF THE PREFERRED EMBODIMENTS

The inventors have recognized that the pulmonary circulation and the pulmonary light scattering properties may be significantly modified in a large variety of cardio-pulmonary patho-physiological conditions and diseases, and that such information may be of significant diagnostic and therapeutic importance. The embodiments described herein are designed to monitor the functionality of the arteries and veins in the lungs, as well as the integrity and functionality of the lung tissues that surround them, using Doppler ultrasound. It is referred to herein as "Transthoracic Pulmonary Doppler" or "TPD".

Figure 1:
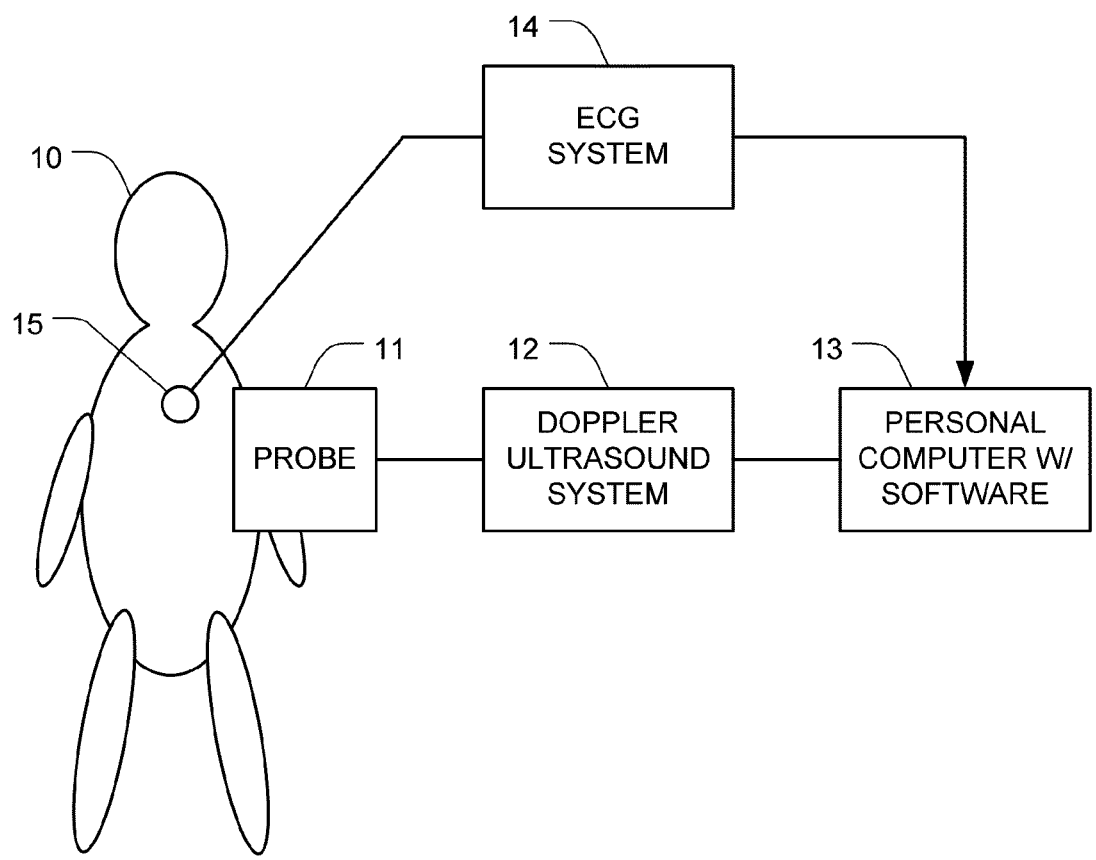
FIG. 1 is a block diagram of an embodiment of a Transthoracic Pulmonary Doppler ("TPD") System.

FIG. 1 is a block diagram of one such embodiment. A Doppler ultrasound machine 12 in conjunction with the probe 11 (which includes an ultrasound transducer) is used to determine the power at every relevant velocity in a target region of the subject 10, over time, in a conventional manner. This may be accomplished by generating pulsed ultrasound beams, picking up the reflected energy, calculating the Doppler shifts, and processing the data thus obtained to provide the matrix of power and corresponding velocities of the ultrasound reflectors. One example of a suitable Doppler ultrasound machine 12 is the Sonara/tek pulsed Trans-Cranial-Doppler device (available from Viasys, Madison, Wis., US), which is a pulsed Doppler system. The Doppler ultrasound machine 12 sends the data that it captures to a personal computer 13 that is loaded with software to generate a conventional Doppler ultrasound display (e.g., on a monitor associated with the computer 13) in which the x axis represents time, the y axis represents velocity, and power is represented by color. Suitable software for controlling the ultrasound parameters is also available from Viasys. Note that in alternative embodiments, the functions of the Doppler ultrasound machine 12 and personal computer 13 may be combined into a single device.

Preferably, an ECG system 14 is also provided. The ECG system 14 interfaces with conventional ECG leads 15 and generates an output in any conventional manner. The output is preferably synchronized in time with the Doppler ultrasound machine 12 so that both an ECG and ultrasound display can be displayed on the same time scale. The output of the ECG system 14 is provided to the personal computer 13 in any conventional manner. In alternative embodiments, it may be combined by the Doppler ultrasound machine 12 instead.

A standard TCD probe such as a 21 mm diameter, 2 MHz sensor with a focal length of 4 cm may be used as the probe 11. Suitable probes are available from Viasys for use with their Sonara/tek machines. Conventional probes for making Doppler ultrasound measurements of peripheral or cardiac blood vessels may also be used. These applications, however, typically use narrow beams, often shaped using a phased array transducer, to provide a high spatial resolution that is helpful for making geometrical characterization of the relatively small targets. While these narrow beams can produce usable results in the context of TPD, some preferred alternative embodiments use relatively wide beams, for example beams with an effective cross section of at least ½ cm (e.g., between ½ and 3 cm). This may be accomplished by using a smaller transducer, and by using single element transducers instead of phased array transducers that are popular in other anatomical applications. When a wider beam is used, the system can take advantage of the fact that the lungs contain relatively large complexes of unspecified geometrical shape consisting of blood vessels (both arteries and veins) and their surrounding lung tissues.

Note that since imaging the lung with ultrasound is impossible because of the scattering, one has to scan for targets without guidelines, except for the known anatomy. Note also that scattering lowers the advantage of scanning by either phase array or by mechanical means. Furthermore, since the whole lung depth induces scattering, CW (continuous wave) ultrasound is less effective than PW (pulsed wave) Doppler ultrasound for pulmonary applications. Therefore, some preferred embodiments utilize PW ultrasound with relatively wide beams. Optionally, such embodiments may employ multiple sensors positioned on the surface of the body.

Optionally, specially selected or designed ultrasound probes and/or suitable beam power control may be used, including dynamic adjustable beam shape and size so as to enable measurement from variable tissue volumes. Note that in contrast to when Doppler is used for other tissue targets, here the average and integral of signals originating from relatively large volumes contain valuable information.

In addition to the standard software for generating a display from the Doppler signals, the personal computer 13 preferably includes software for activating the TPD and selecting the desired operating mode, display mode, and storage modes. The personal computer 13 also includes or has access to appropriate data storage resources (e.g., local or remote hard drives). The personal computer 13 preferably processes the original velocity-and-power vs. time data using one or more noise reduction (NR) algorithms that are optimized to minimize the noise created by the signal scattering and attenuation by the lung tissue.

One preferred approach to noise reduction involves two phases—averaging and edge detection. In the first phase, an averaged signal from a number of cardiac cycles is obtained by averaging the power/velocity data of N characteristic signals, where each of the N signals preferably represents a single cardiac cycle. N is preferably an integer between 4 and 20 (e.g., 10). Preferably, each signal is bounded by an R-wave at each end, although in alternative embodiments other points on the cardiac cycle may be used as a time reference point. The calculated averaged signal is assumed to characterize the spectrogram behavior for the subject, and therefore is the basis on which the relevant features are later determined. Note that while it is preferable to perform this averaging phase, in alternative embodiments this phase could be skipped and subsequent processing could be performed on data from a single cardiac cycle.

The second phase is edge detection and envelope calculation. In this phase, we delineate, in regards to both amplitude and time, the power and velocity signal tracings vs. time, and thereby separate the sections that represent the blood vessel movement (i.e., the signal) from the noise. One or more noise reducing algorithms may be used during this phase. In one preferred embodiment, two specific edge detection algorithms, referred to herein as algorithm A and algorithm B, are applied to the data. Both algorithm A and algorithm B are applied on the averaged signal and calculate the edge (i.e., envelope) between the signal and the noise in the averaged image.

Algorithm A is a local, one-dimensional method in which the edge ($e_A$) between signal and noise at a given time is defined according to the statistics of the data at the proximity of this time only. This algorithm includes two steps: In the first step, we define, at any given time (ti), a threshold 'thr(ti)' for each power spectrum A(ti) by searching for a region of lowest energy in the proximity of ti. We then set thr(ti) to be equal to the highest power level in this region. Next, we apply thr(ti) on A(ti) and deem all parts of A(ti) above thr(ti) as corresponding to movement regions and all other parts as corresponding to noise.

In the second step of Algorithm A, we refine the initial distinction between flow and noise by using the statistics of noise: In this step, we assume down estimation (flow being included in noise region); adjust envelopes detection to exclude flow pixels from noise regions; and identify pixels of flow in noise regions by their relatively high values. Symbolically, this can be represented by the following three steps:

(a) For each t={1, 2, . . . N}, calculate P(t)={mean of A(t) in noise region}
(b) Define a threshold 'thr2' which is based on the mean of {P(1), P(2), . . . P(N)}
(c) For each t' where P(t')>thr2, reduce P(t') by raising upper envelope or lowering the lower envelope until P(t')<=thr2. For better results, steps (a)-(c) are preferably repeated a number of time (e.g., 10 times).

Algorithm B is an edge detection algorithm that treats the data as two-dimensional image. In this method, the signal is seen as an object surrounded by noise which is segmented out of it, and the edge ($e_B$) is calculated accordingly. This segmentation method is an implementation of the Chan-Vese algorithm. (See Chan T. F., Vese L. A., Active contours without edges. Image Processing IEEE, Transactions on, Volume 10, Issue 2: 266-277 (February 2001), which is incorporated herein by reference).

The edge calculated by Algorithm A ($e_A$=[$e_A$(t1), $e_A$(t2), . . . ]) is then combined with the edge calculated by Algorithm B ($e_B$=[$e_B$(t1), $e_B$(t2), . . . ]). One suitable approach to combining those two edges is by assuming that the desired edge passes between the two edges that were found. This may be done using a variety of approaches. One approach is take a simple average of the results from algorithm A and algorithm B at each point. Another approach for combining those two edges is to create an array of weights (w=[w(t1), w(t2), . . . ]) as follows: (1) the power levels of the image at the gap are integrated along time; (2) the result is linearly transformed to have a maximal value of '1' and minimal value of '0'; and (3) the output for the edge at a time point ti is then defined by the following equation: e(ti)=w(ti)*$e_A$(ti)+(1−w(ti))*$e_B$(ti).

Figure 2:
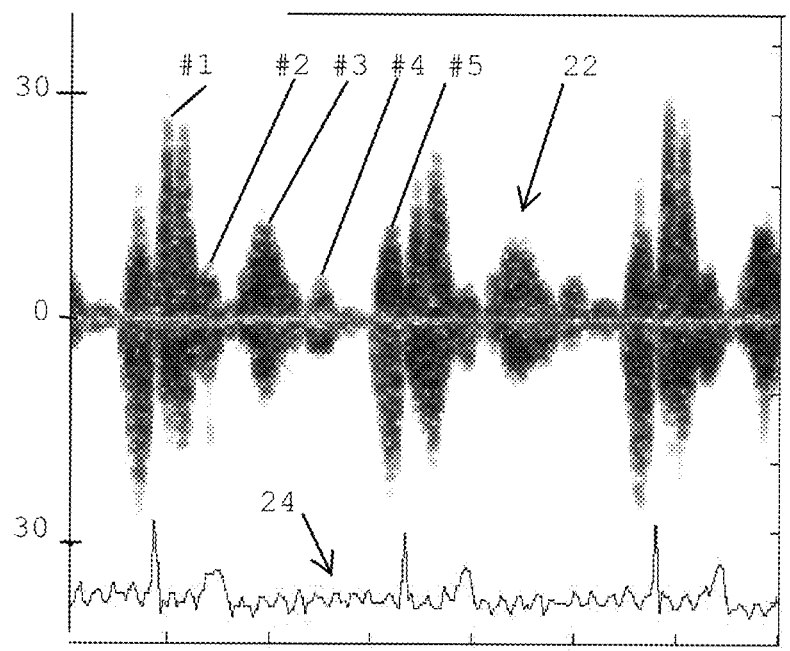
FIG. 2 depicts an example of an output generated by the system of FIG. 1.

The resulting output is preferably smoothened via a one-dimensional median filter (e.g., of order 3) and displayed, and FIG. 2 depicts an example of the resulting output. Note that in alternative embodiments, only one algorithm (i.e., either algorithm A or algorithm B or a different NR algorithm) may be used, either taken alone or combined with other NR algorithms.

FIG. 2 depicts the velocities 22 of the ultrasound reflectors in the right lung of a normal subject obtained using a 2 MHz Doppler ultrasound system with the probe positioned about 3 cm to the right of the sternum and 7 cm up from the level of the tip of the xiphoid bone (about the 4th intercostal space). The ultrasound beam was roughly normal to the chest surface. In FIG. 2, darker regions correspond to higher powers. A conventional ECG 24 is preferably also displayed on the bottom of FIG. 2. Similar recordings were obtained from recordings at depths (gates) of up to 14 cm and from the left lung in areas not dominated by the heart. Maximal signal strength over the right lung was recorded at a depth of 8-9 cm below the surface.

The same pulse repetition frequency (PRF) that is used in conventional TCD systems (i.e., 3-10 kHz) may be used for TPD systems. However, TPD sonograms 22 includes of a number of medium velocity signals that have the same periodicity as the cardiac cycle and usually reach values only up to about 30 cm/sec. Due to these relatively low peak velocities (as compared to Doppler flow measurements in large arteries), the TPD PRF used may be set to a value that is lower than standard pulsed Doppler systems. By lowering the PRF to 1-2 kHz, the effective beam penetration depth is at least doubled as compared with the conventional PRF. This is important as ultrasound velocity in the lung is about 30-50% lower than in fat, muscle etc. thus lowering the effective penetration depth. Preferably, the software is configured to take this lower velocity into account. The transition point where the signals originating in the lung can be detected by recognizing the shallowest point at which the lung signals (i.e., signals with very large returns) appear. Note that measurements from different lung depth result in very similar tracings, and that the traces for other apparently normal subjects had generally similar characteristics.

Figure 3:
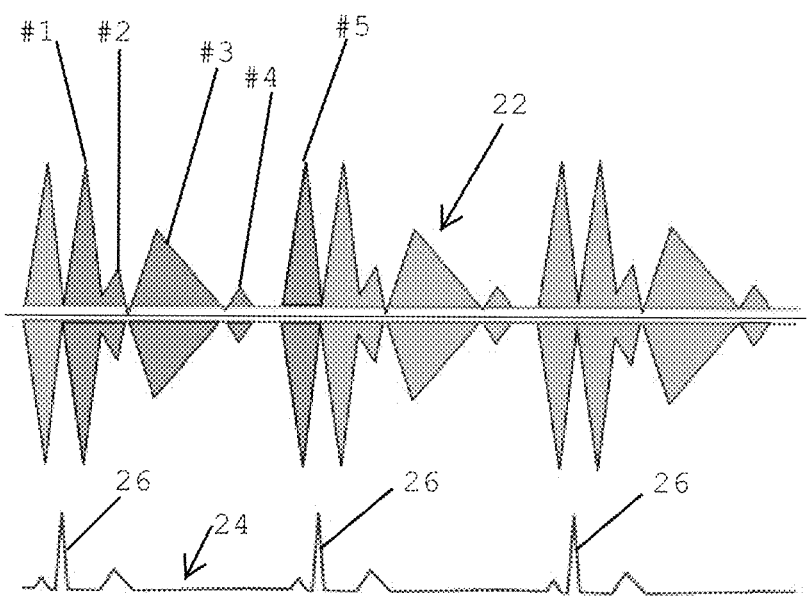
FIG. 3 is a schematically illustration of five features in the output shown in FIG. 2.

It is seen that, at each polarity (positive or negative), one can usually identify five significant features with relatively high energy and a roughly triangular shape. These five features are schematically illustrated and numbered #1-5 in FIG. 3. Each of these features includes a positive component (i.e., positive velocities, indicating that the flow direction is towards the probe) and a corresponding negative component (i.e., negative velocities, indicating that the flow direction is away from the probe), with a high degree of positive/ negative symmetry. Thus, each of these features indicates simultaneous movements in opposite directions. As seen in FIG. 3, these features are synchronous with the cardiac cycle (note the R waves 26 in the ECG 24).

Theory of Operation

The above described signals recorded over the lungs appear to have a unique origin. As is well known the lungs consist of a very large number of alveolar ducts, alveolar sacs and alveoli which can be regarded as miniature gas volumes encapsulated by a very thin membrane. The alveoli, which can be assumed to be reasonably represented by spheroids, have dimensions in the range of 50-150µ. When exposed to ultrasound waves these natural lung components resemble in many respects ultrasound contrast media used in sonography. (Ultrasound contrast agents are gas-filled microbubbles with a high degree of echogenicity, i.e., the ability of an object to reflect the ultrasound waves.) The echogenicity difference between the alveoli and soft tissues is very large and therefore most of the energy is reflected.

Although scattering makes it impossible to obtain ultrasound images of lung structures, it is actually helpful in detecting movement of the highly reflective border between soft tissue and alveoli. Movements of this border are induced by respiration and even more so by cardiac contraction and mechanical pulse waves travelling in the blood and the pulmonary blood vessels. It is well known that the pulmonary blood vessels have a very high compliance (i.e., much larger than that of the systemic circulation), and the air filled alveolar tissue surrounding the vessels is highly compressible. Thus, pressure waves in the pulmonary arteries and veins result in significant changes in their diameter. These changes in turn move the highly reflective border, compressing and moving the alveoli, alveolar sacs, etc. in their vicinity. As the ultrasound propagation velocity in tissue and air are very different, there is a mechanical coupling mismatch at their border resulting in high echogenicity and strong ultrasound reflections, which in this case is from a moving reflector that results in Doppler shifts. These reflections are often on the order of 100 dB above the noise level (in comparison to typical intensities measured from blood flowing in arteries, which are in the range of 30-40 dB above noise level). Because these signals are so strong, the returns are picked up by the Doppler system even though they may be partially masked by a layer of stationary lung tissue, which attenuates ultrasound energy by about 40 dB/cm.

Figure 4A:
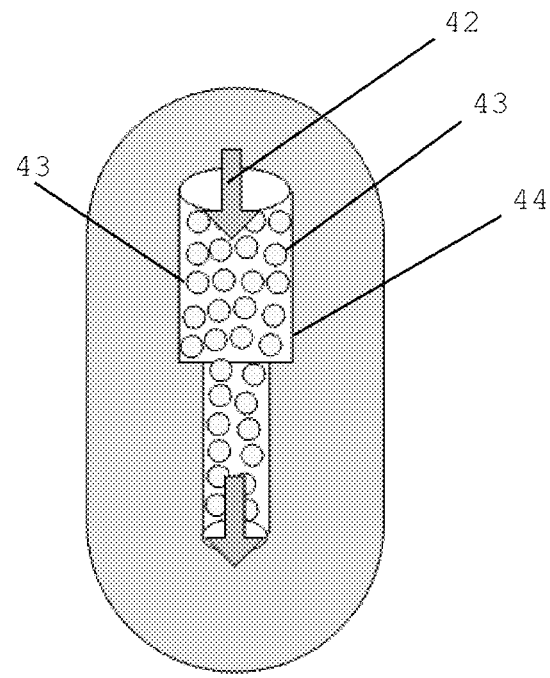
FIG. 4A depicts the "classical Model" of clinical Doppler measurements.
Figure 4B:
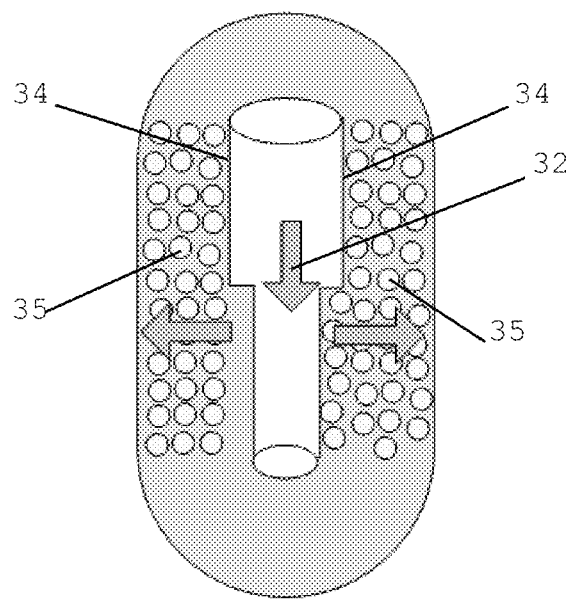
FIG. 4B depicts the origin of the Doppler signals picked up using TPD.

FIG. 4A and FIG. 4B illustrate the differences between conventional Doppler signals and the signals picked up by TPD through the chest wall. FIG. 4A illustrates the "classical Model" of clinical Doppler measurements in which the device measures the Doppler frequency shift resulting from blood flow 42 in arteries and veins, or more specifically from the movement of the erythrocytes 43 (which reflect the ultrasound waves) through those vessels 44.

FIG. 4B illustrates the origin of the Doppler signals picked up using TPD. Here the changes in pressure induce changes in vessel diameter because as the heartbeat generates pressure pulses that urges the blood 32 through the vessel, the vessel walls 34 momentarily bulge outwards and compress the air filled alveoli, alveolar sacs, etc. 35 that surround them. The Doppler shifts of the reflected ultrasound induced by the moving vessel-alveoli border are translated to power-and-velocity vs. time plots and displayed by the TPD system. It is expected that the majority of these signals are generated by small and intermediate size arteries and veins. A unique feature of signals generated in this mode (as opposed to those generated by the flow of blood in the rest of the body) is their bi-directionality. This phenomenon is likely because the lung parenchyma encircles the blood vessels from all sides so that regardless of the relative beam direction, the closer borders move towards the beam source while those at the far side move away from it. As a result, similar signals of opposite polarity are generated. In some cases, as depicted in FIG. 2 the signals seem almost perfectly symmetrical. Such symmetry is rarely seen in non-pulmonary records of blood flow.

It is notable that with conventional Doppler measurements of blood flow through vessels, where the movement is the blood flow itself, the probes are positioned so the ultrasound beam is as parallel as possible to the flow axis to obtain maximal velocity. In contrast, the motion that gives rise to the TPD measurements described herein is perpendicular to the direction of blood flow, so the optimal position is normal to the flow axis and parallel to the vessel radius. But since there are so many blood vessels in the lungs, positioning is less critical in the context of TPD (as compared to conventional Doppler measurements of blood flow through vessels).

Since the features in FIG. 2 always have a repetition cycle corresponding to the R-R interval of the ECG 24, we have concluded that they must originate from structures that reflect ultrasound energy while moving in synchrony with the heart beat. These entities could be the heart itself, the blood flowing in the pulmonary blood vessels, the pulsating blood vessels, or their junctions with alveoli, alveolar sacs, air, etc.

Figure 5A:
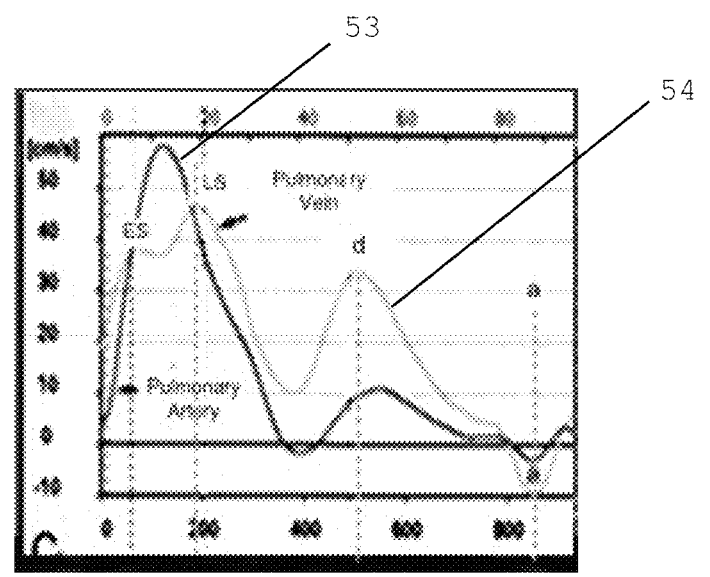
FIG. 5A compares a TPD output of a normal subject with tracings of blood flow velocity in a pulmonary artery and vein.
Figure 5A:
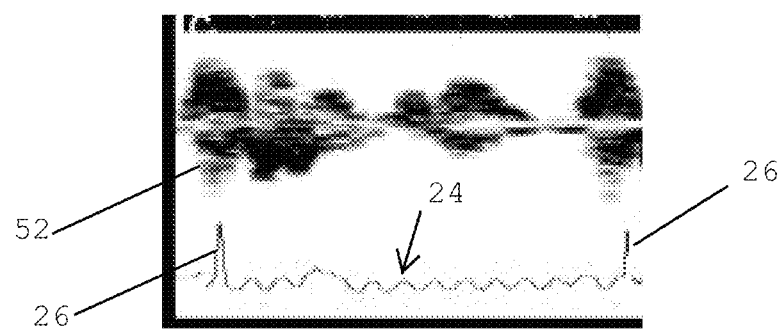

The recorded signals will be referred to as—Lung Doppler Velocity Signals, (LDVS). FIG. 5A compares a typical LDVS 52 of a normal subject with tracings 55, 56 of blood flow velocity in both a pulmonary artery and vein, for a single cardiac cycle, with the cardiac cycle durations normalized to the same time scale (note the R-waves 26 of the ECG 24). Significant correlation is present. FIGS. 5B-E compare the LDVS 56 of normal breathing (FIG. 5B) with those recorded during various respiratory maneuvers over a number of cardiac cycles. For example, during breath-holding at FRC (functional residual capacity) (FIG. 5C), the features 57 have normal shape and velocity but attenuated intensity. During a Valsalva maneuver (FIG. 5D) in which the chest cavity pressure is greatly elevated, the features 58 are seen to virtually disappear. In contrast, during a Muller maneuver (FIG. 5E), which generates negative pressure within the chest cavity, both the velocity and signal power of the LDVS 59 increase.

The synchronization of the five features (#1-5) with the heart beat and associated mechanical events indicates that the signal source is related to pulsations generated by the heart and blood vessels, and the strong modulation of the features by respiratory maneuvers (see FIGS. 5C-E) indicates that the state of the lung parenchyma strongly affects their shape. The fact that similar signals are recorded throughout the lungs, in spite of the strong mechanical dumping properties of the lung parenchyma, rules out direct involvement of the heart and large blood vessels. Thus, it is most likely that the spread of the pulsations is by propagation along the blood vessels in the lungs, including the relatively small ones.

Based on the theory of operation set forth above, we interpret the five features depicted in FIGS. 2 and 3 as follows: Feature #1, which is usually very prominent, appears shortly after the R wave, and coincides with the systolic ventricular contraction. Feature #2, which has lower peak velocity, coincides with the T wave of the ECG and repolarization and ventricular relaxation. Feature #3, which is often double humped and is of relatively longer duration, seems to appear mainly during the diastolic rapid filling phase. Feature #4, which typically has a low peak velocity, corresponds to the diastasis, the latter part of which is often not associated with a detectable signal. Feature #5, which is usually of high peak velocity, coincides with atrial contraction.

The relative amplitudes, rise times and fall times, durations etc. of these five features thus provide information regarding the blood flow hemodynamics, passive mechanical properties of the various cardio-vascular system components, as well as the active (contraction) forces. In addition, the displays provide information related primarily to the pulmonary system.

To verify the theory that the returns are generated by a moving tissue-air boundary, a Doppler sonogram was made using a phantom where pseudo-blood (Doppler test fluid 707, ATS Laboratories Inc. CT, USA) incorporating miniature air bubbles (under 0.5 mm) was flowing in an appropriate vessel. In the sonogram the bubbles appear as bright "blips". The power spectra of the flowing pseudo blood and bubbles reveal that the peak power generated by the moving air bubbles is about 40 dB higher than that of flowing pseudo-blood and coronary flow recorded under similar conditions. These results are compatible with the theory set forth above.

Measurements were taken on 10 normal volunteers aged 27-72 over the right or left lung by means of an ultrasound sensor positioned over the chest wall of a sitting or supine subject. A 21 mm, 2 MHz sensor having a focal length of 4 cm was impedance matched with the chest wall by standard ultrasound gel. Measurements were made from different positions over the chest wall using a pulsed TCD device (Sonara/tek, Viasys, Madison, Wis., USA) at a pulse repetition rate (PRF) of 3 kHz. The transmitted pulse power was up to 10% of the allowed maximal ISPTA.3 (492 mW/cm$^2$). The subjects were connected to a standard three lead ECG (Norav Medical Ltd, Yokneam, Israel) the output of which was included in the display.

Observing the resulting velocity-and-power vs. time traces can provide diagnostic information on the mechanical properties of the pulmonary parenchyma, in general and at specific locations when those traces deviate from the expected normal traces. This may include information related to the tissue structure (which may be relevant to emphysema, fibrosis, atelectasis, etc.), vasculature, or the presence of fluid in or around the alveoli (as in congestive heart failure or pneumonia, vascular events such as emboli & hemorrhage), etc. These deviations from normal can result from changes in the elastic properties as well as the mass of the various tissue elements as well as their spatial distribution. Such changes will result in global or local corresponding changes in the power spectra profiles, time constants, durations, or amplitudes (relative or absolute) of the traces. Physiological manipulations such as deep inspiration, forced expiration, breathe holding, Valsalva maneuvers, exercise, etc. may be used to enhance the diagnostic capabilities. Note that the ultrasound waves reflected from any intra-pulmonary element are modified as they pass through the lung parenchyma that intervenes between them and the chest wall. This tissue acts as a mechanical filter of specific characteristics. These characteristics depend on the state of the relevant parenchyma, such that the power spectra of the signals that pass through this filter reflect on the filter characteristics for acoustic signals as described by Gavriely N., Y. Palti & G. Elroy (Spectral Characteristics of Normal Breath Sounds, J. Appl. Physiol. 50: 307-314 (1981), which is incorporated herein by reference).

Figure 6:
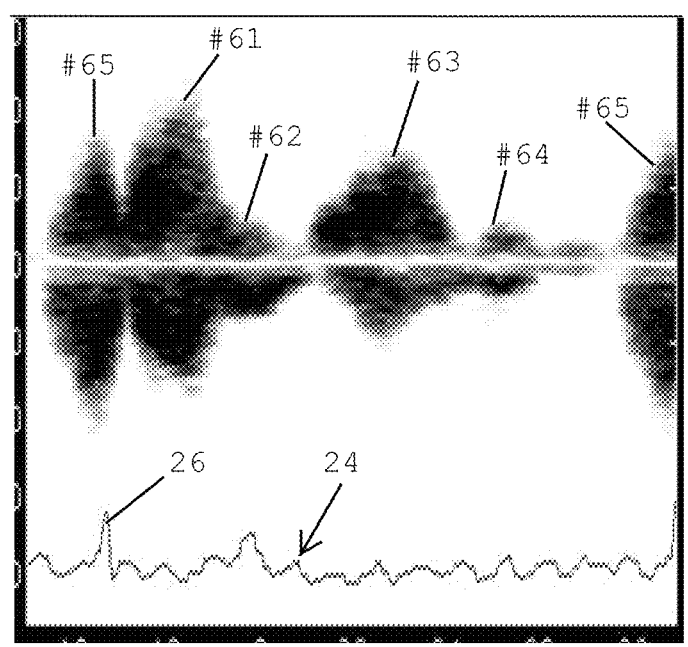
FIG. 6 depicts a TPD output averaged over ten cardiac cycles from a normal subject.

Optionally, the signals from a single subject may be averaged over a number of cardiac cycles using the R wave 26 of the ECG 24 as a reference point. FIG. 6, for example, depicts an average 62 of ten cardiac cycles from a normal subject, recorded over the right lung. Five features #61-65 can be seen, corresponding to features #1-5 discussed above. The traces were generally similar for other normal subjects.

Detection and Characterization of Cardiac Function

One useful application of the TPD system described herein is as a tool for indirectly ascertaining the function of the cardiac system through TPD measurements of the lungs. This is possible because the outcome of the cardiac activities propagate along the pulmonary blood vessels from their origin in the heart to the whole lung volume. A number of clinically significant deviations from normal mechanical cardiac activity can be detected and characterized using TPD in this way, and some examples are given below.

Figure 7A:
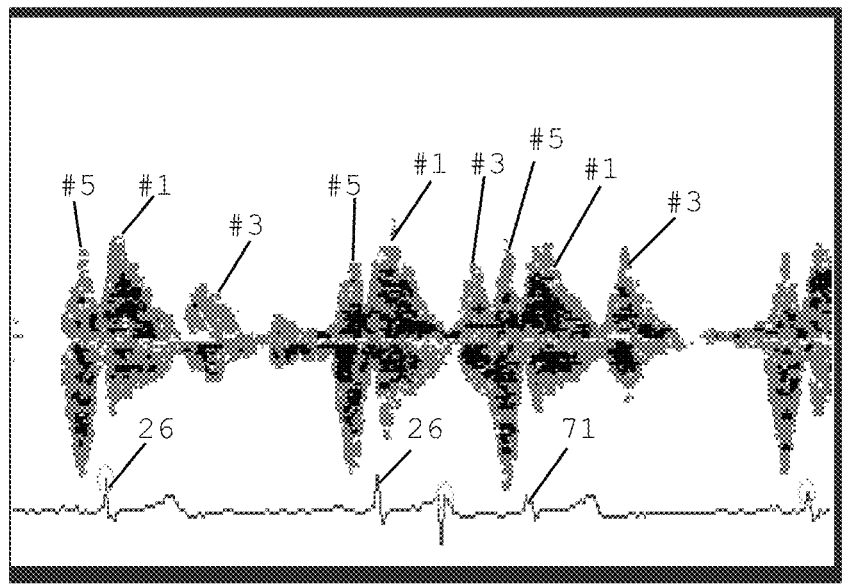
FIG. 7A depicts a TPD output for a normal sinus rhythm followed by a propagating atrial extra-systole.
Figure 7B:
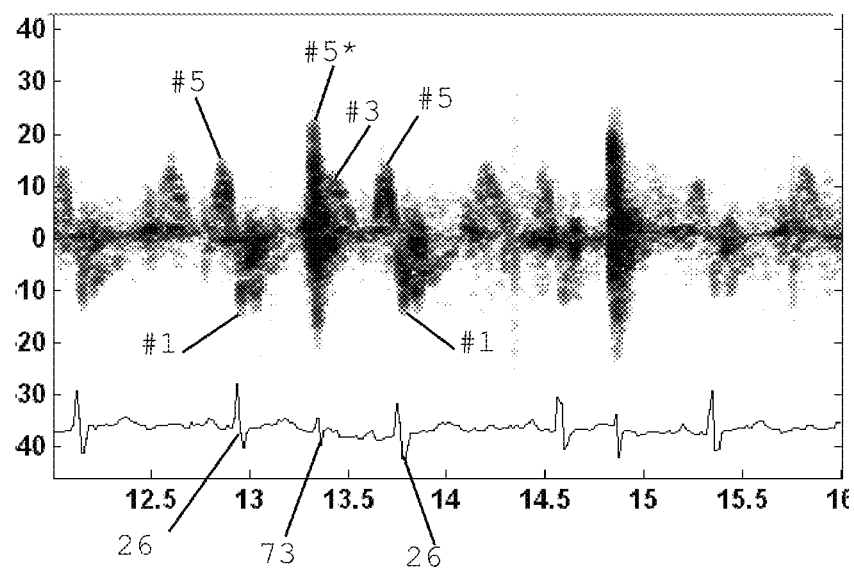
FIG. 7B depicts a TPD output when an atrial non-propagating extra-systole is present.

FIG. 7A depicts the changes from the normal pattern of lung signals in cases of arrhythmia due to atrial extra-systoles, which is a type of additional abnormal cardiac contraction. The left side of FIG. 7A depicts signals typical of a normal sinus rhythm, and the right side depicts the appearance of an atrial extra-systole 71 (i.e., the signals generated by an early electrical beat produced by the sinus node) that propagates to the ventricles. These signals are basically a duplicate of the normal rhythm complex, i.e. they include and extra atrial contraction (feature #5) followed by an extra ventricle contraction (feature #1) and ventricle relaxation (feature #3). When they occur early enough, the atrial contraction signal (feature #5) may superpose in time over previous ventricular relaxation (feature #3). FIG. 7B illustrates the characteristics of a signal produced by an atrial extra-systole 73 resulting in an atrial contraction (feature #5) that does not propagate from the atrium to the ventricles, as manifested by the absence of features #1 and #3 after the abnormal additional feature #5*.

Figure 8:
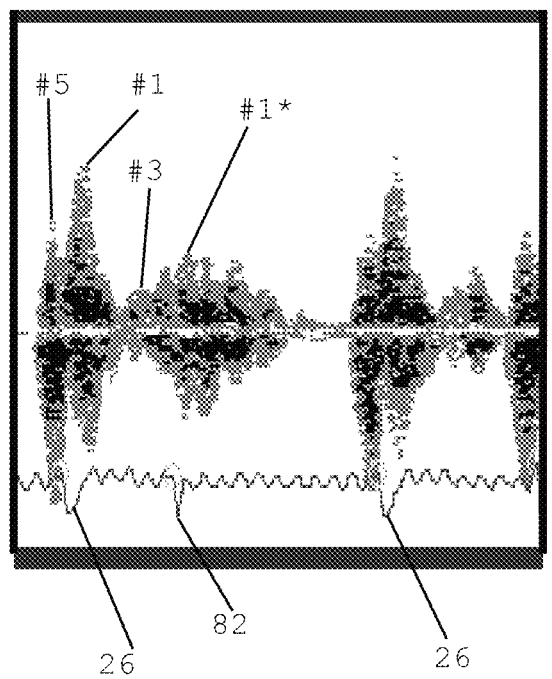
FIG. 8 depicts a TPD output when extra-systolic contractions are present.
Figure 9:
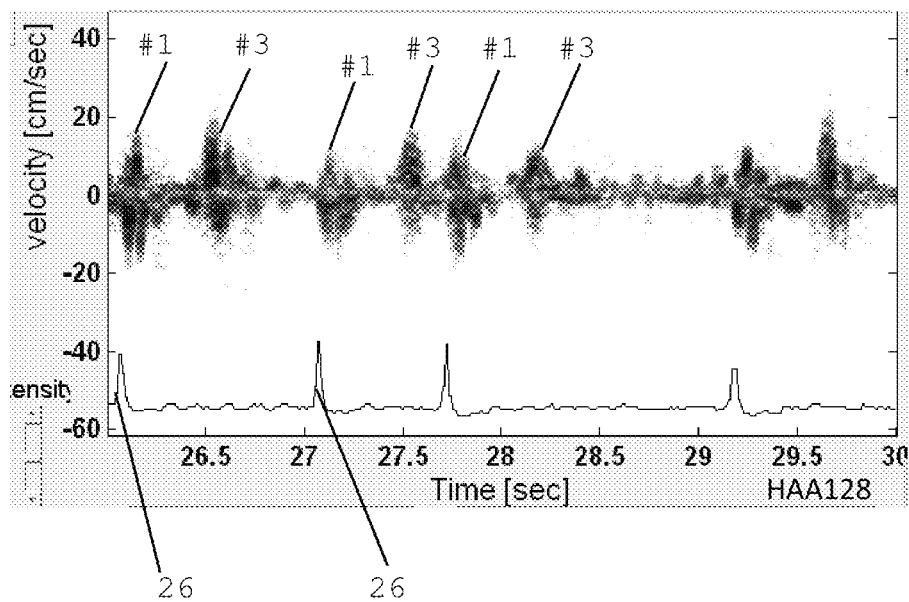
FIG. 9 depicts a TPD output when atrial fibrillation occurs.

FIG. 8 illustrates signals produced by Extra-Systolic contractions (feature #1*) generated by electric abnormal activity 82 in the ventricle. FIG. 9 depicts signals corresponding to contractions of ventricular origin (#1) in a patient suffering from atrial fibrillation. This condition is apparent from FIG. 9 because feature #5 (representing atrial contraction) is missing. It is also seen that the characteristics of the ventricular extra-systoles are very different from those of the atrial extra-systoles, reflecting the large differences of the nature of the mechanical activity. Such recorded tracings can help the physician determine the pathway of propagation of the abnormal activity.

The presence of any of the abnormal features discussed above in connection with FIGS. 7A, 7B, 8, and 9, can therefore be used as an indication that the patient has the corresponding problem. This may be accomplished visually, by looking at the displays and recognizing the relevant features. In alternative embodiments, pattern recognition software may be used to recognize the relevant features automatically.

Multi-Position Measurements

TPD measurements may be taken from different lung depths, and such measurements usually show very similar tracings indicating a wide spread of the signals in the lung volume. Measurements may also be taken from different positions on the subjects' body, such as over the intercostal spaces (e.g. between the 2nd and 3rd ribs or between the 5th and 6th ribs) as well as from positions over the ribs. When such measurements are taken at multiple positions, in some cases there are significant differences between the signal shapes, velocities, and power measurements taken at each position. The inventors have recognized that such recordings in general and specifically recording differences may be used to help diagnose certain physiological conditions.

In one example, measurements were made on two chronic obstructive pulmonary disease (COPD) patients' right lungs at three different positions locations over each patient's right lung: an upper zone at the level of the 2-3 ribs, a middle zone at the level of the 4th rib, and a lower zone at the level of the 5-6 ribs. Unlike the normal subjects in which the measurements taken at the upper, middle, and lower positions were very similar, in the COPD patients the signals at the upper zone were significantly smaller than those in the middle zone, which were in turn significantly smaller than the signals at the lower zone. In addition, the signal shapes (e.g., the degree of symmetry in velocity and power) were also different in the different zones. This deviation from the normal situation can be used as predictor for the presence of COPD. Similarly, other deviations from the normal situation can be used as predictor for the presence of other abnormal conditions.

Figure 10A:
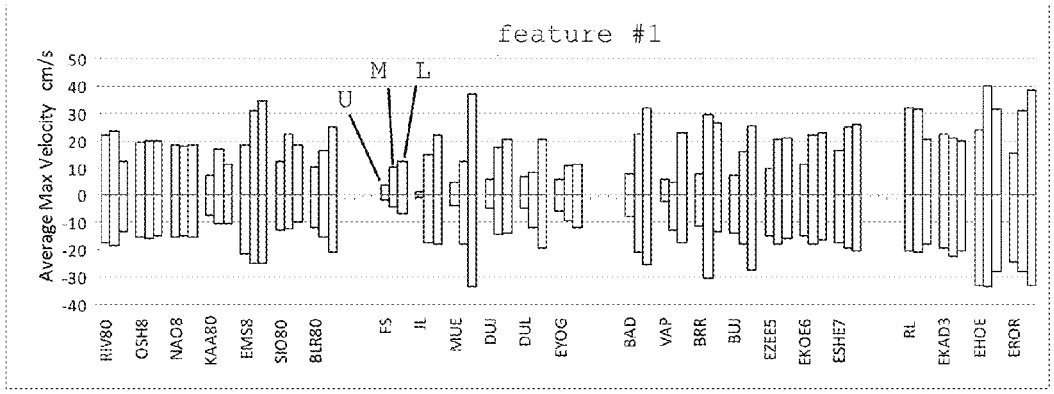
FIGS. 10A-C depict experimental data on the average peak positive and negative velocities for three features of a TPD output.
Figure 10B:
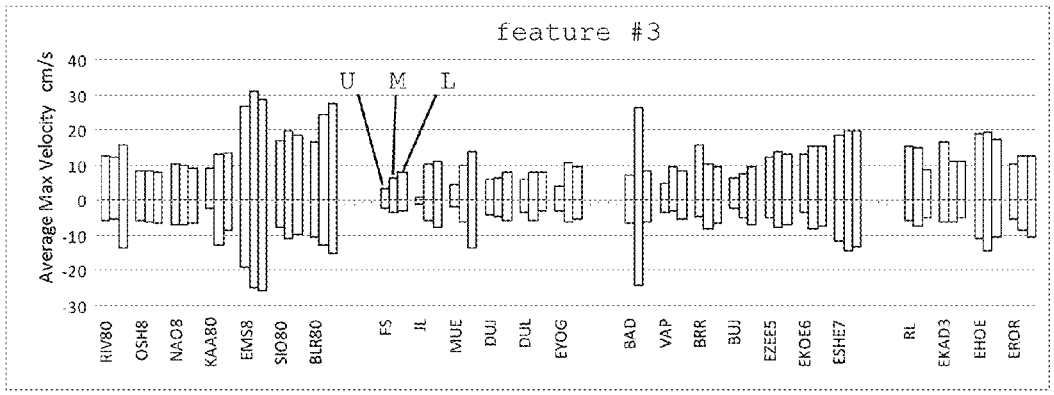
Figure 10C:
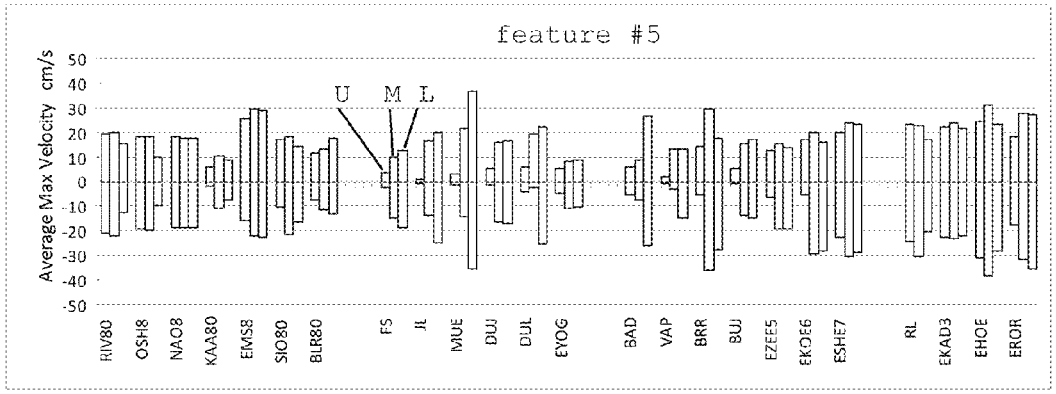

The average peak positive and negative velocities for features #1, 3, and 5 were measured for a group of patients (including normal patients, COPD patients, sarcoidosis patients, and a fibrosis patient) from each of those three positions (i.e., upper, middle, and lower). That experimental data is depicted in FIGS. 10A-C, with positive and negative velocities on the y-axis. The normal patients are the ones on the left, the patients between FS and DUL had COPD, the patients between BAD and BUJ had sarcoidosis, and the patients between RL and EHOE had fibrosis. In FIG. 10A, each group of 3 Bars (left, center, and right) represents the results of the average peak positive and negative velocity (in cm/sec) that was obtained for feature #1 in the upper, middle, and lower zones, respectively, for each patient. FIGS. 10B and 10C depict corresponding data for features #3 and 5. Note that the labels U, M, and L (which denote the upper, middle, and lower zones, respectively) have only been included for one patient in each of FIGS. 10A-C to avoid clutter.

Examination of the data depicted in FIGS. 10A-C reveals that in normal patients, the velocities for feature #1 were roughly similar in all three zones. But in the COPD patients, the velocity was much lower in the upper zone than in the middle zone, and the velocity was much lower in the middle zone than in the lower zone. The same situation was true for feature #5. The presence of those relative velocities for features #1 and 5 can therefore be used as a predictor for the presence of COPD. The test for distinguishing between normal and COPD patients may be fixed (e.g., COPD may be indicated if the peak velocity of the middle reading is at least twice as large as the peak velocity of the upper reading and the peak velocity of the lower reading is at least three times as large as the peak velocity of the upper reading). Alternatively, the threshold levels may be obtained using parameterization as described below. Thus, we see that the differences between the velocities for the features at different locations can be used to help distinguish between normal subjects and patients with various diseases.

Figure 11A:
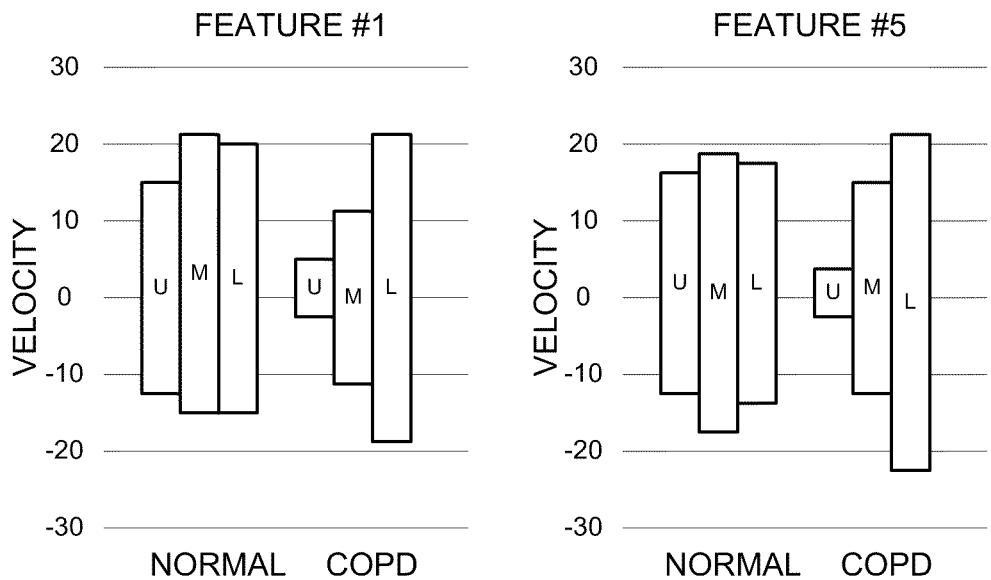
FIG. 11A is a graphical representation of the velocity differences between normal and abnormal subjects.

FIG. 11A is a graphical representation of the differences between normal and COPD subjects, based on the averages of those two groups of patients, which highlights the distinction between the peak velocities for features #1 and #5 at the upper, middle, and lower zones.

Figure 11B:
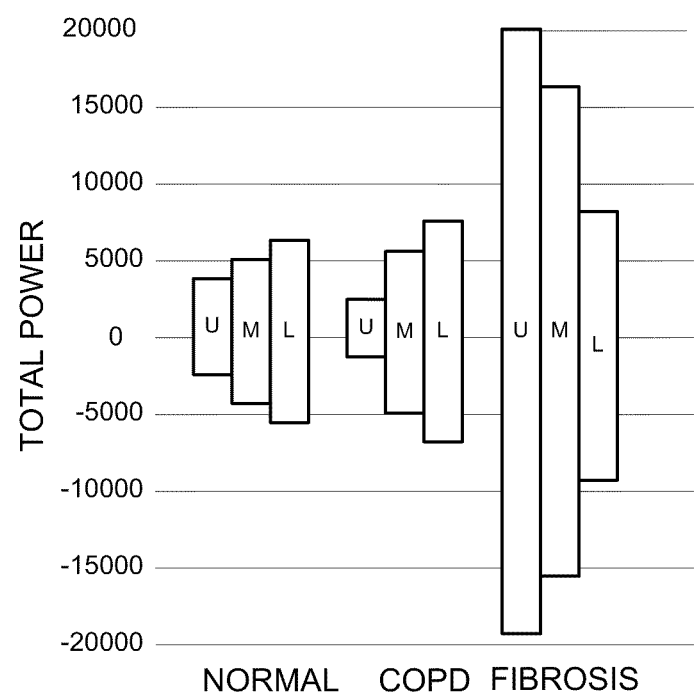
FIG. 11B is a graphical representation of power differences between normal, COPD, and fibrosis subjects.

Optionally, the above described data may be combined with "power sonogram" data, as described in U.S. application Ser. No. 12/771,091, filed Apr. 30, 2010, which is incorporated herein by reference. The personal computer 13 (show in FIG. 1) should then be programmed to extract the power data from the ultrasound returns as described in the '091 application. FIG. 11B demonstrates that power data so obtained can serve to differentiate between normal subjects, patients with COPD, and patients suffering from pulmonary fibrosis. In the latter, connective tissue that conducts ultrasound energy well replaces the air filled alveoli and thus one obtains higher total power values. Note also that in the case of fibrosis (in contrast to the normal and COPD cases) the largest power signal is often recorded from the upper lung segment. This may be used as a predictor for the presence of fibrosis.

Distinctions between the Congestive Heart Failure (CHF), pulmonary emphysema, and edemas can also be characterized by differences their Doppler signatures. For example, in edema patients the power will be lower than normal, but in CHF patients the power may be higher than normal due to the excess fluid in the lungs (which provides less signal attenuation that the air that would ordinarily be there in a normal patient). The power distribution between the different lung zones may be altered with the local changes in the lung parenchyma and vasculature. These distinctions may be detected using TPD and relied on to diagnose those conditions, either visually from the displayed power-and-velocity vs. time displays, or automatically using appropriate pattern recognition or parameterization software. Similar concepts may be used for other pathologies.

Measurement of Pulmonary Blood Pressure

Pulmonary blood pressure may be elevated as a consequence of numerous conditions as well as pulmonary and cardiac diseases such as CHF. Although detection, characterization, and follow up of pulmonary hypertension (PH) is important, all of the prior art technologies are problematic. In some cases, indirect and inaccurate estimation can be made using complex ultrasound imaging. But the only reliable measurement method is invasive—introducing a measuring catheter through the heart into the pulmonary blood vessels. In contrast, TPD can be used to measure the pulmonary blood pressure rapidly, simply, effectively, and non-invasively.

In a classical sphygmomanometer, the pressure around a peripheral artery (e.g., brachial, radial) is elevated while the arterial pulse is being monitored and the maximal and minimal pressure is determined on the basis of the changes in the vessel pulsations. Within this framework the systolic blood pressure is determined by the pressure at which blood flow and pulsations cease. As explained above, the signals recorded by the TPD reflect pulsations in the pulmonary blood vessels. These vessels are surrounded by lung parenchyma that consists of multiple air compartments the pressure of which can be controlled. Because of this, it becomes possible to determine the pulmonary blood pressure by elevating the pulmonary air pressure and monitoring the TPD signals to determine the blood flow and vessel pulsations through the blood vessels in the lungs under various pressure conditions.

Figure 12:
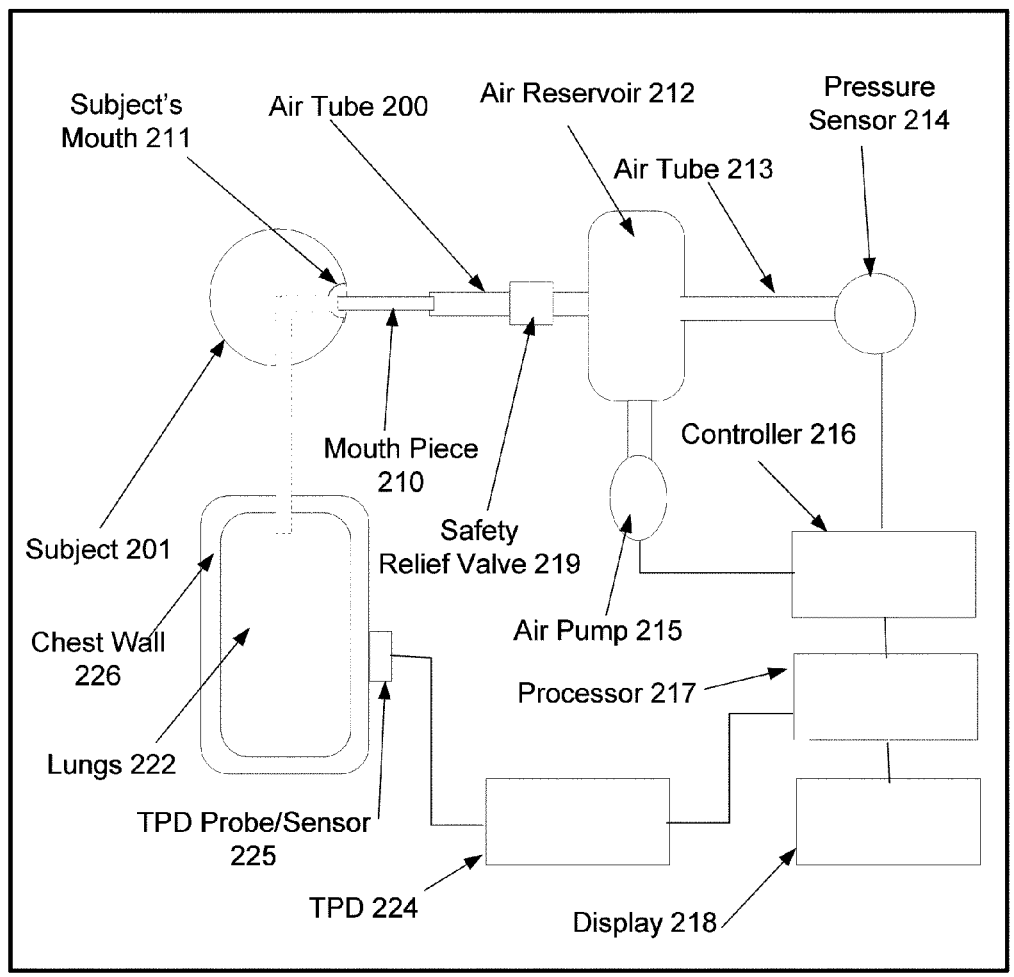
FIG. 12 is a block diagram of system for performing pulmonary blood pressure measurements.

FIG. 12 is a block diagram of a system for performing such a measurement. During the entire procedure, the TPD Probe/sensor 225 should be positioned on the patient's chest 226 and the lung signals are processed by TPD 224 recorded and displayed. To obtain readings, the pulmonary air pressure is elevated and then returned to normal. One way to vary the pulmonary air pressure is to have the patient 201 inflates his lungs to a predetermined degree and then blow forcefully into a tube 200 connected to the air reservoir 212 (e.g., via a disposable mouth-piece 210). In this case, it is mainly the patient's diaphragm that increases the pressure.

The pressure is preferably displayed on display 218 for the patient to see, and the patient is instructed to keep the pressure at a requested level. The patient is also instructed to keep his glottis open so that the pressure equalizes in the whole system. Another way to vary the pulmonary air pressure is to elevate the pressure in the lungs 222 using a pump 215 under control of controller 216 and processor 217 so as to drive the lung pressure to the desired level. Feedback is preferably obtained using a pressure sensor 214. Note that in either situation, the desired pressure level may be varied over time to follow a desired curve (e.g., by first increasing the pressure and then letting it drop slowly).

Figure 13:
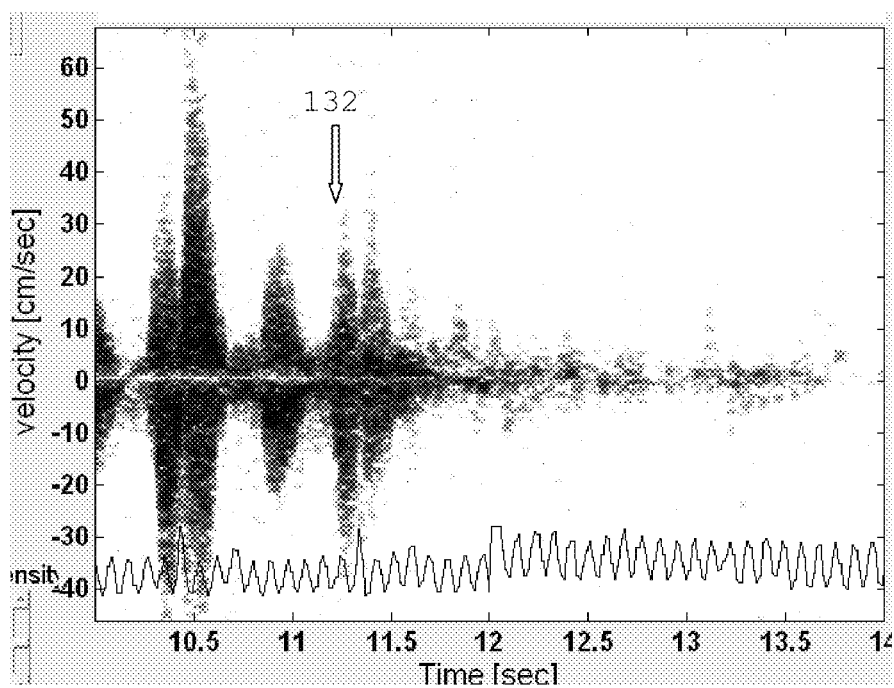
FIG. 13 depicts how the TPD signals change in response to increasing lung air pressure.

FIG. 13 depicts how the TPD signals change in response to a gradual elevation of the lung air pressure, and the resulting changes in the properties of the blood vessels. When the pressure is increased, the blood vessels will eventually collapse (either completely or partially) at the point when the external pressure equals or exceeds the blood pressure, which occurs between 11 and 11.5 seconds in FIG. 13 (denoted by the arrow 132). This phenomenon is similar to the way the blood flow stops when the pressure imposed by a conventional blood pressure cuff pressing on the brachial or radial arteries exceeds a particular level.

Figure 14:
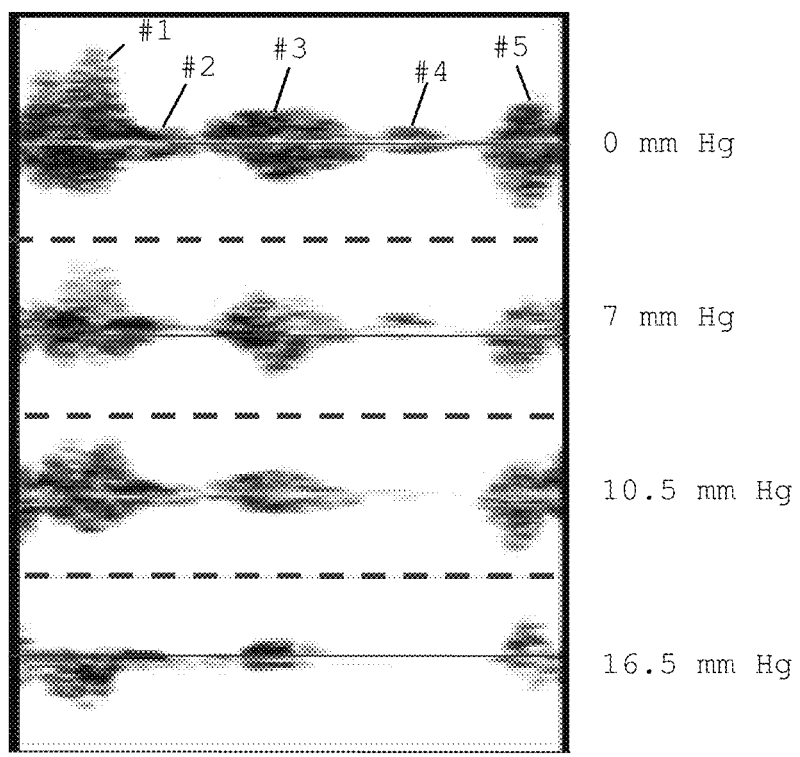
FIG. 14 depicts how the TPD signals differ at different lung air pressures.

FIG. 14 depicts an example of changes that occur in a patient when the lung air pressure is elevated and maintained at the elevated level. The changes in the amplitude and characteristics of the different features (#1-5, discussed above) at the pressure levels indicated at the right carry information regarding the various levels of the blood pressure in the relevant vessels. Note that the variations of each of the five features #1-5 may occur at different pressures. For example, the positive part of signal #1 disappears at a pressure of about 16 mm Hg, while the negative signal, 1\*, remains practically intact. The negative part of signal #3 (3\*) is already attenuated at a pressure of about 10 mm Hg, while the positive part is only attenuated at higher pressures. Signal #4 is also practically eliminated at a pressure of 10 mmHg.

Note that normal pulmonary blood pressures (as measured by invasively introducing pressure sensors into the relevant blood vessels) is usually quoted as 10-15 mm Hg for the diastolic and 25-30 and for the systolic pulmonary artery pressure, and about 8-10 mm Hg for the pressures at the venous side (pulmonary vein) of the pulmonary circulation. But since these values are for the main large vessels into which the pressure transducers are introduced, the lower pressure levels in the TPD-based measurements make sense because the pressures in the smaller vessels are most likely lower (although they have yet not been documented). One can therefore relate the pressures measured using TPD to the appropriate elements of the pulmonary circulation.

Figure 15:
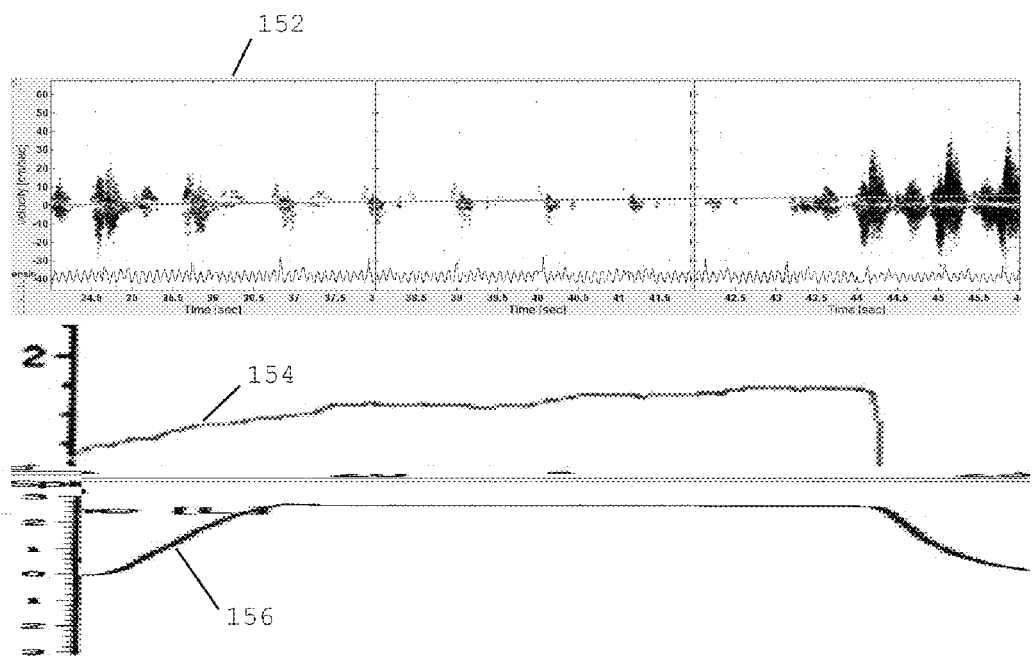
FIG. 15 depicts how the TPD signals change in response to changes in lung air pressure.

The lung air pressure may be elevated gradually in order to record, in a single pressurization, the variation of the features #1-5 under a range of pressures. An example of such a measurement is given in FIG. 15, in which the pressure was slowly increased, then maintained at a high plateau of about 2 kPa, as depicted in the middle panel 154. The recovery of the blood flow through the small pulmonary vessels in response to a decrease in pressure can be seen on the right section of the top panel 152. Note that the pressure elevation in this example involved a lung inflation to a total lung capacity of 3 L, as measured by spirometry, as depicted in the lower panel 156.

The interpretation of the above described signal changes and the determination of the lung circulation pressures can be made by the physician based on when the various TPD features #1-5 shrink or disappear. Alternatively, suitable pattern recognition software may be used to automatically detect the relevant changes.

Figure 16:
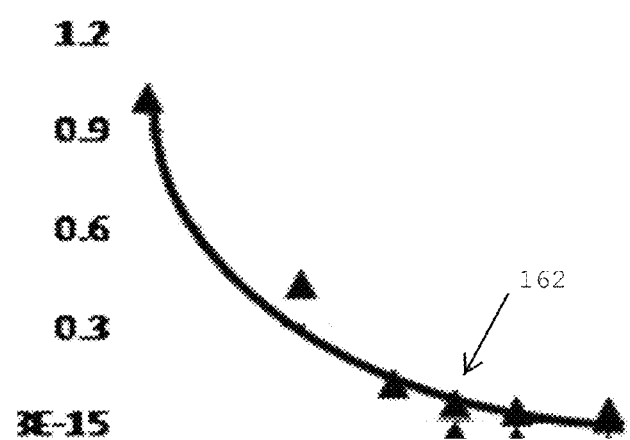
FIG. 16 depicts how the TPD power levels change in response to changes in lung air pressure.
Figure 17A:
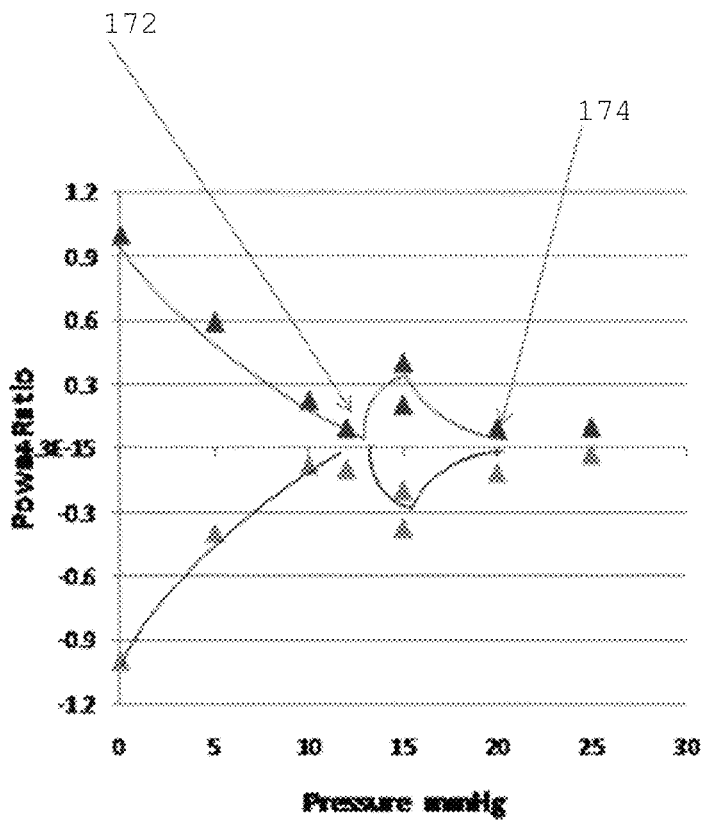
FIG. 17A illustrates that the power level reaches zero at two different pressures.

FIG. 16 depicts the power level of the signals the TPD records when the pulmonary pressure is elevated. The pulmonary vascular bed pressure may be determined from the point 162 the power amplitude approaches zero. FIG. 17A depicts the situation when the pressure is elevated to different levels and maintained these for relatively long periods of time (e.g., 10-20 sec). The signals attenuate as described and approach zero at the pressure level corresponding to that of the venous circulation (12 mm Hg in the example depicted). At a new pressure elevation, for example to 15 mm Hg in the FIG. 17A, the blood flow and pulsations stop. However, as blood flow stops, the pressure drop along the circuit nulls so that the whole system gradually attains the high systolic pressure and all the vessels are reinflated and therefore with time (determined by the capacity of the vasculature) the blood flow and the pulsations reappear. This is seen in the corresponding measured power points in FIG. 17A. Such pulsations will be recorded until a pressure elevation to a value equal to or exceeding the systolic arterial pressure is applied and maintained. The pressure where there are no pulsations whatsoever corresponds to the pulmonary arterial systolic pressure. Thus, there are two points where the curve approaches the zero power level. The first point 172 where the curve approaches the zero power level (i.e., with a pressure reading of about 12 mm Hg for this subject) is believed to correspond to the pulmonary pressure at the venous side. The second point 174 where the curve approaches the zero power level (i.e., with a pressure reading of about 20 mm Hg) is believed to correspond to the pulmonary pressure at the arterial side.

Figure 17B:
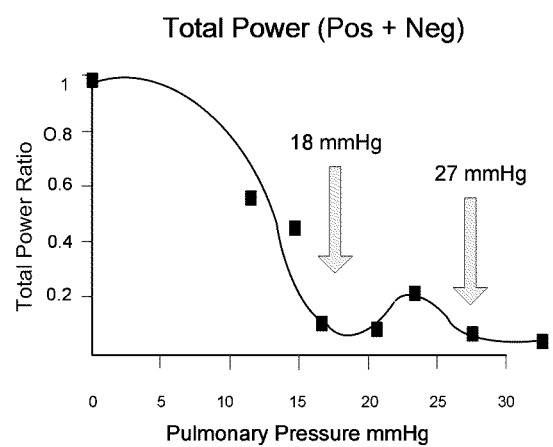
FIG. 17B depicts a power reading for a normal subject.
Figure 17C:
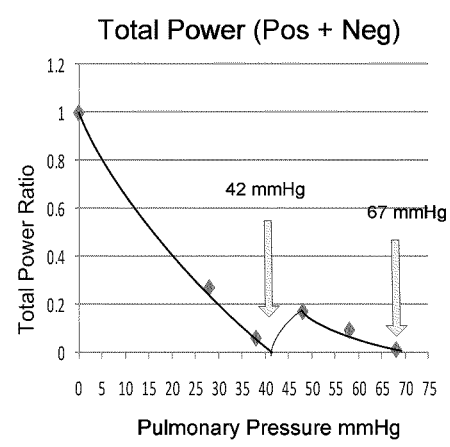
FIG. 17C depicts a power reading for a subject with pulmonary hypertension.

FIGS. 17B and 17C compare the power readings for a normal subject (FIG. 17B) and a subject with pulmonary hypertension (FIG. 17C). The higher pressure readings are evident in the hypertension subject.

Automatic Feature Recognition

Figure 18:
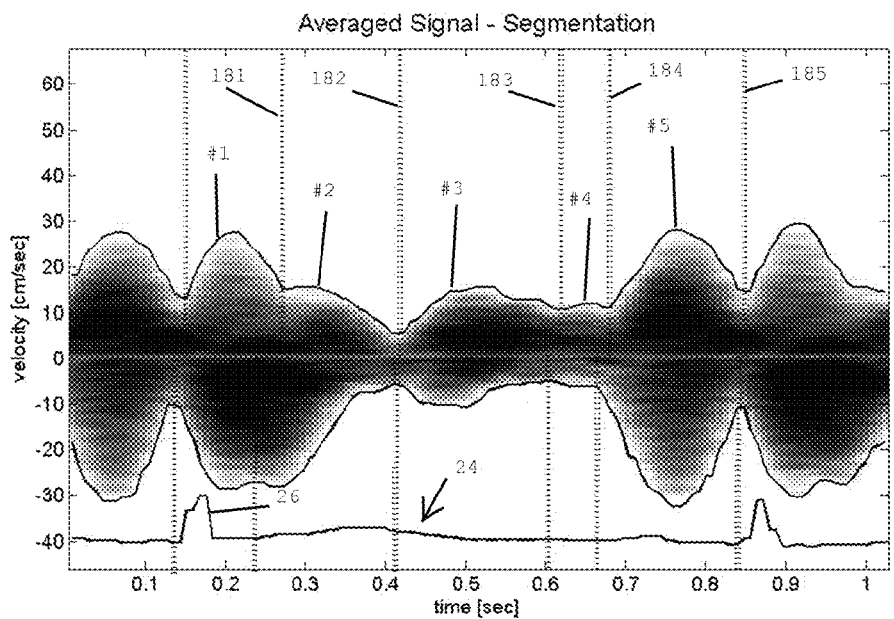
FIG. 18 depicts the boundaries between features determined by an automatic feature recognition algorithm.

The discussion above makes frequent references to features #1-5. Optionally, software that recognized the delineation between each of those features may be implemented in the personal computer 13 (shown in FIG. 1). Automatic feature recognition ("AFR") may be implemented on the averaged signals discussed above in connection with FIG. 6, on a single signal (e.g., as depicted in FIG. 2), or after the averaging operation contained within the NR (i.e., the first phase of the noise reduction routine discussed above). FIG. 18 is an example of automatic feature recognition based on the latter. In FIG. 18, each of the features #1-5 is bounded by two local minimum points on the calculated envelope, and defined according to the relative location of its peak velocity (i.e., maximum point) and the averaged signals' ECG waveforms. These local minima define the transitions 181-185 between the various features and are denoted by dashed lines in FIG. 18. In a regular cardiac rhythm, the features are defined in relation to the ECG signal 24 as follows: #1—the segment with the first velocity peak after the first R-wave 26; #2—the segment with the first velocity peak after feature #1 but preceding the ECG's T-wave; #3—the segment with the first velocity peak after the T-wave ends; #4—the segment bounded between feature #3 and feature #5; and #5—the segment with the velocity peak that immediately precedes the next R wave and next feature #1.

AFR can be useful because the absolute and relative calculated parameters that characterize these segments may be used to classify and diagnose a pathology and its location.

These parameters are useful for automated recognition of various conditions that rely on parameterization, discussed below.

Parameterization

Parameterization may be used to characterize the various features so as to diagnose and estimate the extent of various pathologies such as COPD, Sarcoidosis, Fibrosis asthma, emphysema, pulmonary hypertension, pulmonary embolism, tumors, arteriosclerosis of pulmonary vessels, atelectasis, cardiac contractile dysfunction, and arrhythmia etc. Quantification of the various parameters may be done on specific segments and the relations between them, as well as on the variability of the signals in the original spectrogram (i.e., before it was averaged). The parameterization may be implemented using the approaches described in U.S. application Ser. No. 12/700,828 ("the '828 application"), filed Feb. 5, 2010, which is incorporated herein by reference.

Some of the data is derived from the power spectra themselves as provided by the Doppler measurements. The features of these power spectra may also be parameterized, for example the power at specific velocities, the average slopes of the curves, the number of different slopes at the positive and negative features etc. Parameters may also be derived from the velocity and power versus time tracings. The tables below contain examples of parameters that may be used to parameterize the TPD results, and their definitions:

Velocity Features:

$\text{peak\_velocity}\{PDS_i\} = \max(\text{envelope}\{PDS_i\})$ $\text{peak\_velocity\_ratio}\{PDS_{i,j}\} = \dfrac{\text{peak\_velocity}\{PDS_i\}}{\text{peak\_velocity}\{PDS_j\}}$ $\text{max\_slope}\{PDS_i\} = \max\left\{\dfrac{d}{dt}(\text{envelope}\{PDS_i\})\right\}$ $VTI\{PDS_i\} = \Delta t \cdot \sum\limits_{PDS_i} \text{envelope}\{PDS_i\}$ $ADPV\{PDS_i\} = \dfrac{1}{t2 - t1 + 1} \sum\limits_{PDS_i=t1}^{t2} \text{envelope}\{PDS_i\}$ $\text{std\_peak\_velocity}\{PDS_i\} = \text{std}(\text{peak\_velocity}\{PDS_{orig\_i}\})_{(PDS_{orig\_j}) \in cycles\_before\_averaging}$ $\text{Mean\_weighted\_V} = \dfrac{\sum\limits_{t=t1}^{t2} \sum\limits_{v=0}^{\text{envelope}(t)} (P_{(t,v)} \cdot v)}{\sum\limits_{t=t1}^{t2} \sum\limits_{v=0}^{\text{envelope}(t)} P_{(t,v)}}$ $\text{MMWVC} = \dfrac{\Delta t \cdot \sum\limits_{t=t1}^{t2} \left( \dfrac{\sum\limits_{v=0}^{\text{envelope}(t)} (P_{(t,v)} \cdot v)}{\sum\limits_{v=0}^{\text{envelope}(t)} P_{(t,v)}} \right)}{t2 - t1 + 1}$ Power Features:

$\text{Mean\_power} = \text{mean}\{P_{(t,v)}\}_{(t,v) \in PDS\_i}$
$\text{Max\_power} = \max\{P_{(t,v)}\}_{(t,v) \in PDS\_i}$ Power Features:

$\text{Median\_power} = \text{median}\{P_{(t,v)}\}_{(t,v) \in PDS\_i}$
$\text{std\_power\_flow} = \text{std}\{P_{(t,v)}\}_{(t,v) \in PDS\_i}$
$\text{std\_power\_flow\_dB} = \{10 \cdot \log_{10}(P_{(t,v)} + 1)\}_{(t,v) \in PDS\_i}$ $PVTI = \Delta v \cdot \Delta t \cdot \sum\limits_{t=t1}^{t2} \sum\limits_{v=0}^{\text{envelope}(t)} (P_{(t,v)} \cdot v)$ $\text{total\_power} = \Delta v \cdot \Delta t \cdot \sum\limits_{t=t1}^{t2} \sum\limits_{v=0}^{\text{envelope}(t)} P_{(t,v)}$ Time Features:

$PDS\_duration = \{t_{end} - t_{start}\}_{(t) \in PDS\_i}$
$PDS\_ECG\_synchronization = \text{abs}(t(\max\_velocity\{PDS_i\}) - t(\max(R/T - \text{wave})))_{(t,v) \in ROI}$ $\text{duration\_percentage} = \left( \dfrac{PDS\_duration}{(t_{end} - t_{start})_{(t) \in averaged\_cycle}} \right)_{(t,v) \in ROI}$ Other Features Age
Weight
Sex
Height Using these parameters, the learning and classifying steps may be implemented as described in the '828 application.

CONCLUSION

The Doppler signatures of the following of tissues and structures may change with pathology: pulmonary emphysema, pulmonary emboli, pulmonary hypertension, pulmonary blood vessel stenosis & malformations, conditions associated with pulmonary fibrosis, pneumonia, atelectasis, pneumothorax, congestive heart failure, pulmonary solid tumors, various cardiac malfunctions that are manifested in the pulmonary blood vessels, tumors, and foreign bodies, etc. Thus, the lung Doppler signals picked up using TPD may be used to provide insights and potentially valuable diagnostic information regarding the structure and integrity of the lung parenchyma and vasculature. TPD may therefore serve as a new non-invasive and non-destructive tool for diagnosis of pulmonary disease & function. It may also enable continuous monitoring of the status of a failing pulmonary or cardio-vascular system, and help determine the efficacy and so enable dose calibration, for optimal treatment.

An additional unique diagnostic capability of the TPD is to determine the compliance (elastance) of the pulmonary vascular tree components that changes in cases of arteriosclerosis and other vascular conditions. Vascular compliance can be measured on the basis of the pulse propagation velocity in the vessel because the more rigid the vessel is, the faster the propagation will be. In the case of the lungs, the propagation velocity can be determined from the delay between the time of appearance of any of the lung signals (or their peak, etc.), at different locations along the propagation pathway. Such delay measurements can be made, manually or automatically by appropriate software, in the different records obtained at different lung locations or at different depths beneath a single location.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of evaluating the functionality of a patient's heart or lung, the method comprising the steps of: transmitting ultrasound energy into the patient's lung; detecting Doppler shifts of reflected ultrasound induced by moving borders between blood vessels in the lung and air filled alveoli that surround the blood vessels, wherein movement of the borders between blood vessels in the lung and air filled alveoli that surround the blood vessels is caused by pressure waves in the blood vessels that result in changes in diameter of those blood vessels; processing the detected Doppler shifts with an algorithm designed to increase signal from the moving borders between blood vessels in the lung and air filled alveoli that surround the blood vessels with respect to other reflected ultrasound signals and outputting processed power and velocity data;
   wherein the algorithm comprises the steps of:
   (a) calculating P(t)={mean of the power spectrum A(t) in noise region} for each time t={1, 2, . . . N};
   (b) defining a threshold 'thr2' based on the mean of {P(1), P(2), . . . P(N)}; and
   (c) reducing P(t') by raising upper envelope or lowering the lower envelope until P(t')<=thr2, for each t' where P(t')<thr2;
   and displaying the outputted power and velocity data.

2. The method of claim 1, further comprising the step of diagnosing a condition of the patient's heart based on a result of the displaying step.

3. The method of claim 1, further comprising the step of diagnosing a condition of the patient's lung based on a result of the displaying step.

4. The method of claim 1, further comprising the step of displaying an ECG that is aligned in time with the data displayed in the displaying step, using a common time scale.

5. The method of claim 1, wherein the processing step implements a Chan-Vese algorithm.

6. A method of evaluating the functionality of a patient's heart or lung, the method comprising the steps of:
   transmitting ultrasound energy into the patient's lung for a period of time that corresponds to at least one cardiac cycle;
   detecting Doppler shifts of reflected ultrasound induced by moving borders between blood vessels in the lung and air filled alveoli that surround the blood vessels, wherein movement of the borders between blood vessels in the lung and air filled alveoli that surround the blood vessels is caused by pressure waves in the blood vessels that result in changes in diameter of those blood vessels;
   processing the detected Doppler shifts with at least one noise reduction algorithm designed to increase signal from the moving borders between blood vessels in the lung and air filled alveoli that surround the blood vessels with respect to other reflected ultrasound signals and outputting processed power and velocity data;
   wherein at least one noise reduction algorithm comprises the steps of:
   (a) calculating P(t)={mean of the power spectrum A(t) in noise region} for each time t={1, 2, . . . N};
   (b) defining a threshold 'thr2' based on the mean of {P(1), P(2), . . . P(N)}; and
   (c) reducing P(t') by raising upper envelope or lowering the lower envelope until P(t')<=thr2, for each t' where P(t')<thr2;
   displaying, on a display, the processed power and velocity data for the period of time; and
   correlating an abnormality in at least one of (a) a feature on the display that corresponds to systolic ventricular contraction, (b) a feature on the display that corresponds to ventricular relaxation, (c) a feature on the display that corresponds to a diastolic rapid filling phase, (d) a feature on the display that corresponds to diastasis, and (e) a feature on the display that corresponds to atrial contraction with an abnormal condition of the patient's heart or lung.

7. The method of claim 6, wherein the abnormality is that at least one of the features is absent.

8. The method of claim 6, wherein the abnormality is the presence of a feature that corresponds to extra-systole.

9. The method of claim 6, wherein the abnormality is that at least one of the features occurs at an incorrect time.

10. The method of claim 6, further comprising the step of displaying an ECG that is aligned in time with the data displayed in the displaying step, using a common time scale.

11. The method of claim 6, wherein the at least one noise reduction algorithm further comprises the step of implementing a Chan-Vese algorithm.

12. The method of claim 6, further comprising the step of averaging the ultrasound power and velocity data for a plurality of cardiac cycles, wherein the averaging step is performed prior to the displaying step.

13. A method of evaluating the functionality of a patient's heart or lung, the method comprising the steps of:
   transmitting ultrasound energy into the patient's lung for a period of time that corresponds to at least one cardiac cycle;
   detecting Doppler shifts of reflected ultrasound induced by moving borders between blood vessels in the lung and air filled alveoli that surround the blood vessels, wherein movement of the borders between blood vessels in the lung and air filled alveoli that surround the blood vessels is caused by pressure waves in the blood vessels that result in changes in diameter of those blood vessels;
   processing the detected Doppler shifts with at least one noise reduction algorithm designed to increase signal from the moving borders between blood vessels in the lung and air filled alveoli that surround the blood vessels with respect to other reflected ultrasound signals and outputting processed power and velocity data;
   wherein the at least one noise reduction algorithm comprises the steps of:
   (a) calculating P(t)={mean of the power spectrum A(t) in noise region} for each time t={1, 2, . . . N};
   (b) defining a threshold 'thr2' based on the mean of {P(1), P(2), . . . P(N)}; and
   (c) reducing P(t') by raising upper envelope or lowering the lower envelope until P(t')<=thr2, for each t' where P(t')<thr2;

checking for abnormalities in (a) a feature of the processed power and velocity data that corresponds to systolic ventricular contraction, (b) a feature of the processed power and velocity data that corresponds to ventricular relaxation, (c) a feature of the processed power and velocity data that corresponds to a diastolic rapid filling phase, (d) a feature of the processed power and velocity data that corresponds to diastasis, and (e) a feature of the processed power and velocity data that corresponds to atrial contraction; and correlating an absence of abnormalities in the checking step with a normal condition of the patient's heart or lung.

14. The method of claim 13, further comprising the step of displaying an ECG that is aligned in time with the data displayed in the displaying step, using a common time scale.

15. The method of claim 13, wherein the at least one noise reduction algorithm further comprises the step of implementing a Chan-Vese algorithm.

16. The method of claim 13, further comprising the step of averaging the ultrasound power and velocity data for a plurality of cardiac cycles, wherein the averaging step is performed prior to the displaying step.

* * * * *